US00PP34015P2

(12) United States Plant Patent
Lim

(10) Patent No.: US PP34,015 P2
(45) Date of Patent: Mar. 15, 2022

(54) ***HIBISCUS* PLANT NAMED 'ALTEARLYBIRD'**

(50) Latin Name: *Hibiscus rosa-sinensis*
Varietal Denomination: ALTEARLYBIRD

(71) Applicant: Altman Specialty Plants, Inc, Vista, CA (US)

(72) Inventor: Peter Lim, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/356,852

(22) Filed: Jun. 24, 2021

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

*Primary Examiner* — June Hwu
(74) *Attorney, Agent, or Firm* — Cassandra Bright

(57) ABSTRACT

A new and distinct cultivar of *Hibiscus* plant named 'ALTEARLYBIRD' is disclosed, characterized by golden orange-yellow blooms with magenta base. Plants have a low growing, upright habit, and dark, narrow, glossy foliage that is resistant to leaf spot disease. Flowering is early and continuous. The new variety is a *Hibiscus*, typically produced as an ornamental plant.

1 Drawing Sheet

Latin name of the genus and species: *Hibiscus rosa-sinensis.*

Variety denomination: 'ALTEARLYBIRD'.

BACKGROUND OF THE INVENTION

The new *Hibiscus* cultivar is a product of a planned breeding program conducted by the inventor, Peter Lim. The objective of the breeding program was to produce vigorous *Hibiscus rosa-sinensis* cultivars with healthy foliage. The cross resulting in this new variety was made Jul. 1, 2012.

The seed parent is the unpatented *Hibiscus rosa-sinensis* 'Luau Lilikoi Yellow'. The pollen parent is the unpatented variety *Hibiscus rosa-sinensis* 'Spin the Bottle'. The new variety was identified and selected as a potentially interesting selection in September 2014. Selection was made at a commercial nursery in Vista, Calif.

Asexual reproduction of the new cultivar 'ALTEARLYBIRD' was first performed on Sep. 11, 2014 in Vista, Calif., by vegetative cuttings. Subsequent propagation has shown that the unique features of this cultivar are stable and reproduced true to type in successive generations.

SUMMARY OF THE INVENTION

The cultivar 'ALTEARLYBIRD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTEARLYBIRD'. These characteristics in combination distinguish 'ALTEARLYBIRD' as a new and distinct *Hibiscus* cultivar:

1. Golden orange-yellow blooms with magenta base.
2. Early blooming.
3. Low growing, upright plant habit.
4. Constant flowering.
5. Dark green, glossy foliage that is resistant to leaf spot disease.

PARENT COMPARISONS

Plants of the new cultivar 'ALTEARLYBIRD' are similar to the seed parent 'Luau Lilikoi Yellow', in most horticultural characteristics. However, characteristics of the new cultivar differ in the following:

1. The new variety blooms earlier than the seed parent.

Plants of the new cultivar 'ALTEARLYBIRD' are similar to the pollen parent 'Spin the Bottle', in most horticultural characteristics. However, characteristics of the new cultivar differ in the following:

1. Flowers of the new variety have more evenly spaced and formed petals.
2. The new variety blooms earlier than the pollen parent.

COMMERCIAL COMPARISON

Plants of 'ALTEARLYBIRD' are similar in some horticultural characteristics to the variety *Hibiscus* 'Social Butterfly', unpatented. The new variety, however, differs in the following:

1. Flowers of 'ALTEARLYBIRD' are smaller than flowers of 'Social Butterfly'.
2. Plants of 'Social Butterfly' have a taller growth habit than 'ALTEARLYBIRD'.
3. Flowers of 'ALTEARLYBIRD' are orange-yellow with a magenta base, while flowers of 'Social Butterfly' are pink, fuchsia, yellow, and white.

Plants of 'ALTEARLYBIRD' are similar in some horticultural characteristics to the variety *Hibiscus* 'Early Spring', unpatented. The new variety, however, differs in the following:

1. Flowers of 'ALTEARLYBIRD' are smaller than flowers of 'Early Spring'.
2. Plants of 'Early Spring' have a taller growth habit than 'ALTEARLYBIRD'.
3. Flowers of 'ALTEARLYBIRD' are orange-yellow with a magenta base, while flowers of 'Early Spring' are pink with a yellow edge, and white eyes.

BRIEF DESCRIPTION OF THE PHOTOGRAPH

The accompanying photograph illustrates in full color a typical flower of 'ALTEARLYBIRD' from a plant grown outdoors at a commercial nursery in Vista, Calif. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'ALTEARLYBIRD' plant. This plant was grown at a commercial nursery in Vista, Calif. The growing temperature ranged from about 7° C. to 30° C. during the day and from about 5° C. to 12° C. during the night. No artificial light, photoperiodic treatments were given to the plants. Measurements and numerical values represent averages of typical plant types.

Botanical classification: *Hibiscus rosa-sinensis* 'ALTEARLYBIRD'.

PROPAGATION

Typical method: Hardwood stem cuttings.

Root description: Roots are fine, fibrous and well branched. Tan/brown in color, not effectively measured with a color chart.

PLANT

Plant type: Tender, woody flowering shrub.

Age of plant described: Approximately 2 years old.

Growth habit: Upright and compact.

Height: 50 cm.

Plant spread: 68 cm.

Branching characteristics: 2 to 4 breaks from a pinch, occurring at acute angles.

Length of primary lateral branches: 15 to 35 cm.

Quantity of lateral branches: About 8 to 12.

Characteristics of primary lateral branches:

*Diameter.*—Average range 9 mm to 15 mm.

*Color.*—New growth near RHS Green 143B, flushed Greyed-Purple 183B, mature growth near RHS Greyed-Green 197B, striated Grey-Brown N199A.

*Texture.*—New growth very slightly hirsute, older growth striated.

Internode length: 2 to 3 cm.

FOLIAGE

Leaf:

*Arrangement.*—Alternate.

*Quantity.*—Approximately 20 per branch.

*Average length.*—8 to 9 cm, excluding petiole.

*Average width.*—6 to 7 cm.

*Shape of blade.*—Obovate.

*Apex.*—Rounded.

*Base.*—Obtuse.

*Margin.*—Entire, few very shallow and infrequent crenations toward apex.

*Texture of top surface.*—Glabrous.

*Texture of bottom surface.*—Glabrous.

*Color.*—Young foliage upper side: RHS Green 137A. Young foliage under side: RHS Green 137C. Mature foliage upper side: RHS Green 137A. Mature foliage under side: RHS Green 137B.

*Venation.*—Type: Pinnate. Venation color, upper side: RHS Green 138A. Venation color, under side: RHS Yellow-Green 144A.

*Petiole.*—Length: 3 to 3.5 cm. Diameter: 3 to 4 mm. Color: RHS Green 137B, base flushed Greyed-Purple 183A. Texture: Upper surface very slightly pubescent, lower surface glabrous.

*Stipule.*—Shape: Narrow deltoid. Length: 5 to 6 mm. Width: 3 mm. Color: Upper side: Near RHS Green 138B. Upper side: Near RHS Green 138C. Texture: Slight rough pubescence.

FLOWER

Natural flowering season: Late Spring through Summer.

Flower type and habit: Solitary, rotate.

*Single, double, multiplex.*—Single.

*Petals overlapping.*—Strongly overlapping.

Rate of flower opening: 1 to 2 days from bud to fully opened flower.

Flower longevity on plant: 1 to 2 days.

Persistent or self-cleaning: Self-cleaning.

Bud:

*Shape.*—Ovate.

*Length.*—5 cm.

*Diameter.*—2.2 cm.

*Color.*—RHS Yellow-Green 145C, lightly flushed Red 51C.

Flower size:

*Diameter.*—12 cm.

*Depth.*—7 cm.

Petals:

*Quantity.*—5.

*Arrangement.*—Whorled, strongly overlapping, changing to moderately overlapping at full maturity.

*Length.*—9 cm.

*Width.*—8 cm.

*Shape.*—Broad spatulate.

*Apex.*—Obtuse rounded with moderate ruffles and shallow crenations.

*Base.*—Attenuate.

*Margin.*—Entire, moderate ruffling.

*Texture, upper and lower surfaces.*—Smooth, slightly rugose on lower half.

*Color.*—When opening, upper surface: RHS Orange 24A, basal blotch (forming flower eye) Red-Purple 58A, flushed N57A. When opening, lower surface: RHS Orange 25B, basal blotch faintly flushed Red-Purple 59C. Fully opened, upper surface: RHS Yellow-Orange 23A, flushed 22A. Basal blotch (forming flower eye) Red 53C, flushed N57A. Fully opened, lower surface: RHS Orange 26B, flushed 26A. Basal section, flushed near Red 54C, faint streaks near Red-Purple 61A. Ratio of basal blotch/eye to petal size: About 20% of petal blade blotched. Feathering color: RHS White 155A. Feathering size: Slight, about 15 mm long.

Sepals:

*Quantity.*—5.
*Length.*—2.0 cm.
*Width.*—2 cm.
*Shape.*—Ovate.
*Margin.*—Entire.
*Apex.*—Acute.
*Base.*—Fused.
*Color.*—Upper surface: RHS Yellow-Green 144B. Lower surface: RHS Green 143C.
*Texture.*—Lower surface very short hirsute, upper surface glabrous.

Epicalyx:

*Quantity of bracts.*—5.
*Bract length.*—1.5 cm to 2 cm.
*Bract width.*—5 to 7 mm.
*Bract shape.*—Narrow deltate.
*Bract margin.*—Entire.
*Color.*—RHS Yellow-Green 144B upper surface, Green 143B lower surface.
*Texture.*—Glabrous all surfaces.

Peduncles:

*Length.*—5.5 cm to 7 cm.
*Diameter.*—3 to 4 mm.
*Angle.*—Approximately 45° to the lateral branch.
*Strength.*—Strong.
*Texture.*—Roughly pubescent.
*Color.*—RHS Yellow-Green 144A. Very small basal flush near Greyed-Purple 187A.

Fragrance: None.

REPRODUCTIVE ORGANS

Stamens:

*Number.*—About 50.
*Filament length.*—4 to 6 mm.
*Filament color.*—Near RHS Red 52C.

Anthers:

*Shape.*—Irregular sphere.
*Length.*—About 2 mm.
*Color.*—Near RHS Yellow 9A.
*Pollen color.*—Near RHS Orange 26A.
*Pollen amount.*—Scant.

Pistil:

*Number.*—1.
*Length.*—7 cm.
*Style.*—Length: 6.8 cm. Color: Lower section near RHS Red-Purple N57B, upper section near Red-Purple 58D. Highly iridescent throughout.
*Stigma.*—Shape: Peltate. Color: Near RHS Red 46A.
*Ovary color.*—Near RHS Yellow-Green 145C.

OTHER CHARACTERISTICS

Seeds: Not observed.

Disease/pest resistance: Observed resistance to leaf spot disease(assumed *Pseudomonas syringae*). No other resistance nor susceptibility to normal diseases and pests of *Hibiscus rosa-sinensis* have been observed.

Temperature tolerance: USDA Zones 8 through 11.

What is claimed is:

1. A new and distinct cultivar of *Hibiscus* plant named 'ALTEARLYBIRD' as herein illustrated and described.

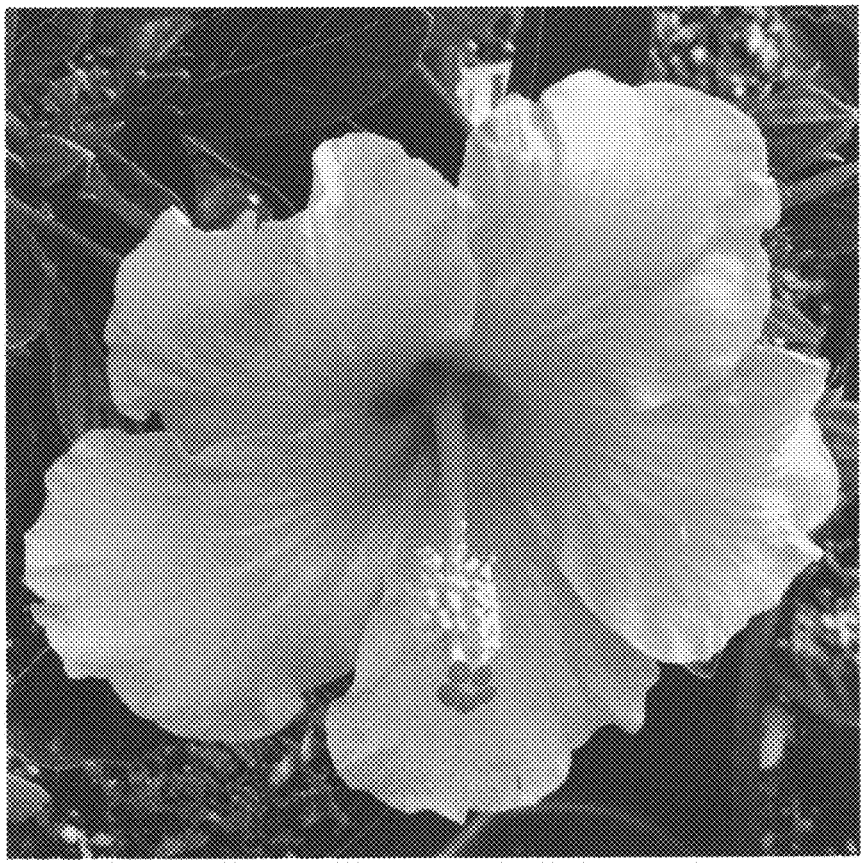

* * * * *